(12) United States Patent
Cutchins

(10) Patent No.: US 11,399,979 B2
(45) Date of Patent: Aug. 2, 2022

(54) APPARATUS FOR REMOVING DEBRIS FROM AN ORGAN

(71) Applicant: Linwood Cutchins, Edgewater Park, NJ (US)

(72) Inventor: Linwood Cutchins, Edgewater Park, NJ (US)

( * ) Notice: Subject to any disclaimer, the term of this patent is extended or adjusted under 35 U.S.C. 154(b) by 609 days.

(21) Appl. No.: 14/489,962

(22) Filed: Sep. 18, 2014

(65) Prior Publication Data

US 2015/0073360 A1    Mar. 12, 2015

(51) Int. Cl.
| | | |
|---|---|---|
| *A61F 9/007* | (2006.01) | |
| *A61M 1/00* | (2006.01) | |
| A61H 9/00 | (2006.01) | |
| A61H 23/00 | (2006.01) | |

(52) U.S. Cl.
CPC .......... *A61F 9/00709* (2013.01); *A61M 1/84* (2021.05); *A61H 9/00* (2013.01); *A61H 23/00* (2013.01); *A61M 1/882* (2021.05); *A61M 2210/0612* (2013.01)

(58) Field of Classification Search
CPC . A61F 9/00709; A61M 1/008; A61M 1/0096; A61M 2210/0612; A61H 9/00; A61H 23/00

USPC ........................................................ 604/315
See application file for complete search history.

(56) References Cited

U.S. PATENT DOCUMENTS

| | | | |
|---|---|---|---|
| 4,798,599 A | 1/1989 | Thomas | |
| 5,106,139 A | 4/1992 | Palmer et al. | |
| 5,290,082 A | 3/1994 | Palmer et al. | |
| 6,264,259 B1 * | 7/2001 | Fortune | B25B 11/007 294/186 |
| 2004/0073144 A1 * | 4/2004 | Carava | A61H 9/005 601/6 |
| 2007/0204398 A1 | 9/2007 | Dubois | |
| 2010/0062397 A1 * | 3/2010 | Brewer | A46B 9/045 433/216 |
| 2012/0271272 A1 * | 10/2012 | Hammack | A61F 9/0017 604/500 |

* cited by examiner

*Primary Examiner* — Andrew J Mensh
(74) *Attorney, Agent, or Firm* — Sonya C. Harris; Invention Services Patent Firm

(57) ABSTRACT

An apparatus comprises a vacuum portion being configured for generating a vacuum force for sucking debris. A tube extends a distance from the vacuum portion. The tube is configured for extending the vacuum force for the distance and for carrying the debris sucked by the vacuum force to the vacuum portion for storage therein. An organ engagement portion is joinable to a distal end of the tube. The organ engagement portion is configured for engaging an organ of a user for removal of the debris from a soft tissue of the organ with the vacuum force and without a use of a liquid.

14 Claims, 2 Drawing Sheets

APPARATUS FOR REMOVING DEBRIS FROM AN ORGAN

CROSS-REFERENCE TO RELATED APPLICATIONS

Not applicable.

RELATED CO-PENDING U.S. PATENT APPLICATIONS

Not applicable.

FEDERALLY SPONSORED RESEARCH OR DEVELOPMENT

Not applicable.

REFERENCE TO SEQUENCE LISTING, A TABLE, OR A COMPUTER LISTING APPENDIX

Not applicable.

COPYRIGHT NOTICE

A portion of the disclosure of this patent document contains material that is subject to copyright protection. The copyright owner has no objection to the facsimile reproduction by anyone of the patent document or patent disclosure as it appears in the Patent and Trademark Office, patent file or records, but otherwise reserves all copyright rights whatsoever.

FIELD OF THE INVENTION

One or more embodiments of the invention generally relate to removing debris through suction. More particularly, the invention relates to removing debris from an organ with a cup shaped suction device.

BACKGROUND OF THE INVENTION

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

The following is an example of a specific aspect in the prior art that, while expected to be helpful to further educate the reader as to additional aspects of the prior art, is not to be construed as limiting the present invention, or any embodiments thereof, to anything stated or implied therein or inferred thereupon. By way of educational background, another aspect of the prior art generally useful to be aware of is that eye are the organs of vision. Eyes detect light and convert it into electro-chemical impulses in neurons.

Often, the eye is a complex optical system which collects light from the surrounding environment, regulates its intensity through a diaphragm, focuses it through an adjustable assembly of lenses to form an image, converts this image into a set of electrical signals, and transmits these signals to the brain through complex neural pathways that connect the eye via the optic nerve to the visual cortex and other areas of the brain.

Typically, a vacuum is a space that is devoid of matter, including air pressure. The vacuum is operable to create a sucking pressure through the use of a diaphragm that expands to reduce the pressure within. The reduced pressure creates a partial vacuum, which is filled by air pushed in by atmospheric pressure. This forms a suction in a first direction.

Debris can include any small object that floats in the air. The debris can often get trapped inside an organ, such as the eye. The debris is generally large enough to feel, but difficult to dislodge with fingers or larger instruments.

In view of the foregoing, it is clear that these traditional techniques are not perfect and leave room for more optimal approaches.

BRIEF DESCRIPTION OF THE DRAWINGS

The present invention is illustrated by way of example, and not by way of limitation, in the figures of the accompanying drawings and in which like reference numerals refer to similar elements and in which.

Figure 1:
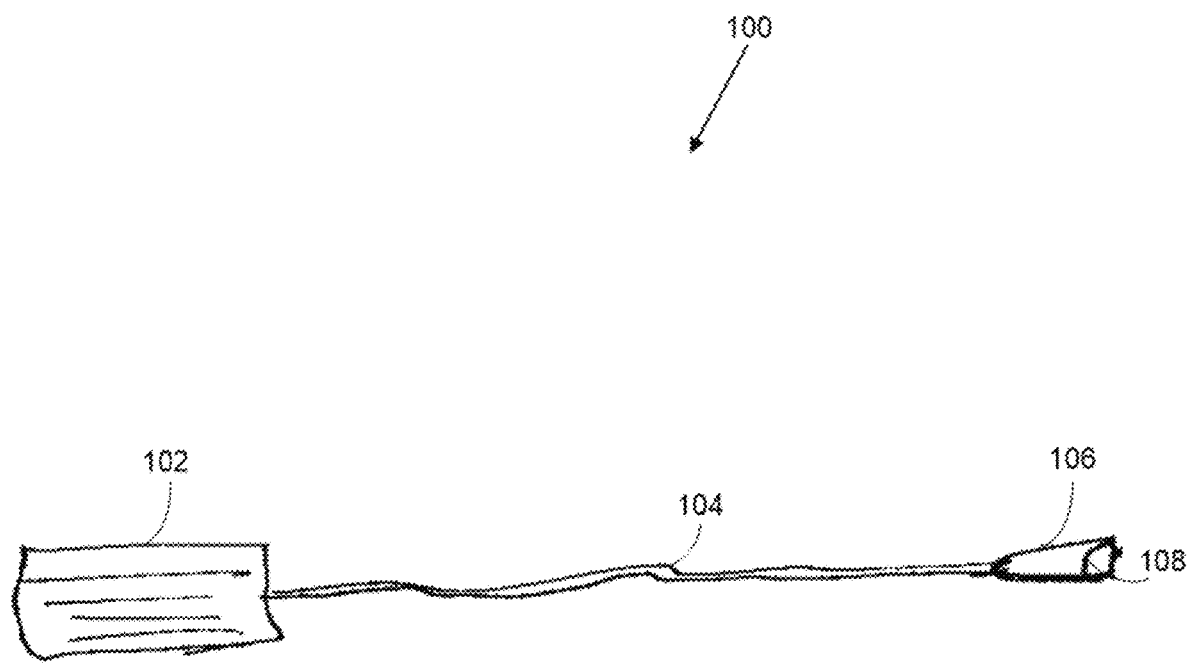
FIG. 1 illustrates a detailed perspective view of an exemplary suction device, in accordance with an embodiment of the present invention.

Unless otherwise indicated illustrations in the figures are not necessarily drawn to scale.

DETAILED DESCRIPTION OF SOME EMBODIMENTS

The present invention is best understood by reference to the detailed figures and description set forth herein.

Embodiments of the invention are discussed below with reference to the Figures. However, those skilled in the art will readily appreciate that the detailed description given herein with respect to these figures is for explanatory purposes as the invention extends beyond these limited embodiments. For example, it should be appreciated that those skilled in the art will, in light of the teachings of the present invention, recognize a multiplicity of alternate and suitable approaches, depending upon the needs of the particular application, to implement the functionality of any given detail described herein, beyond the particular implementation choices in the following embodiments described and shown. That is, there are numerous modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

It is to be further understood that the present invention is not limited to the particular methodology, compounds, materials, manufacturing techniques, uses, and applications, described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" is a reference to one or more steps or means and may include sub-steps and subservient means. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

Unless defined otherwise, all technical and scientific terms used herein have the same meanings as commonly understood by one of ordinary skill in the art to which this invention belongs. Preferred methods, techniques, devices, and materials are described, although any methods, techniques, devices, or materials similar or equivalent to those described herein may be used in the practice or testing of the present invention. Structures described herein are to be understood also to refer to functional equivalents of such structures. The present invention will now be described in detail with reference to embodiments thereof as illustrated in the accompanying drawings.

From reading the present disclosure, other variations and modifications will be apparent to persons skilled in the art. Such variations and modifications may involve equivalent and other features which are already known in the art, and which may be used instead of or in addition to features already described herein.

Although Claims have been formulated in this Application to particular combinations of features, it should be understood that the scope of the disclosure of the present invention also includes any novel feature or any novel combination of features disclosed herein either explicitly or implicitly or any generalization thereof, whether or not it relates to the same invention as presently claimed in any Claim and whether or not it mitigates any or all of the same technical problems as does the present invention.

Features which are described in the context of separate embodiments may also be provided in combination in a single embodiment. Conversely, various features which are, for brevity, described in the context of a single embodiment, may also be provided separately or in any suitable subcombination. The Applicants hereby give notice that new Claims may be formulated to such features and/or combinations of such features during the prosecution of the present Application or of any further Application derived therefrom.

References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

Headings provided herein are for convenience and are not to be taken as limiting the disclosure in any way.

The enumerated listing of items does not imply that any or all of the items are mutually exclusive, unless expressly specified otherwise.

The terms "a", "an" and "the" mean "one or more", unless expressly specified otherwise.

Devices or system modules that are in at least general communication with each other need not be in continuous communication with each other, unless expressly specified otherwise. In addition, devices or system modules that are in at least general communication with each other may communicate directly or indirectly through one or more intermediaries.

A description of an embodiment with several components in communication with each other does not imply that all such components are required. On the contrary a variety of optional components are described to illustrate the wide variety of possible embodiments of the present invention.

As is well known to those skilled in the art many careful considerations and compromises typically must be made when designing for the optimal manufacture of a commercial implementation any system, and in particular, the embodiments of the present invention. A commercial implementation in accordance with the spirit and teachings of the present invention may configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

In the following description and claims, the terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

The present invention will now be described in detail with reference to embodiments thereof as illustrated in the accompanying drawings.

There are various types of suction devices that may be provided by preferred embodiments of the present invention. In one embodiment of the present invention, the suction device may provide a portable device that engages an organ to suck debris from the organ. The organ may include, without limitation, an eye. The device may be configured to engage a section of the organ, such as the cornea of an eye, where the debris resides. Through the use of a vacuum that creates the suction, the device may pull the debris out of a sensitive, soft organ without the use of a liquid to help flush the debris from the organ. The device may be carried and use daily without the need for a physician.

In some embodiments, the device may include a vacuum portion that generates a vacuum for sucking the debris from the organ. The vacuum portion may include an internal diaphragm that expands to reduce the pressure within. The reduced pressure may creates a partial vacuum, which is filled by air pushed in by atmospheric pressure. However in other embodiments, other mechanisms to create the suction may be utilized by the vacuum portion. The vacuum portion may be powered by a power source. A tube may extend from the vacuum section. The tube may be utilized to carry the debris from the organ to a debris storage portion of the vacuum portion.

In some embodiments, an organ engagement portion may join with the organ, generally over a section where the debris resides. The organ engagement portion may include an eye cup. The organ engagement portion may include a rim that is sized and dimensioned to seal the organ engagement portion against the surface of the organ. Those skilled in the art will recognize that a tight seal is necessary to sustain the suction pressure needed to pull the debris from the organ. In this manner, the debris is sucked from the organ, through the tube, and finally into the debris storage portion of the vacuum portion.

FIG. 1 illustrates a detailed perspective view of an exemplary suction device, in accordance with an embodiment of the present invention. In the present invention, a suction device 100 may provide a portable device that engages an organ to suck debris from the organ. The organ may include, without limitation, an eye. The debris may include, without limitation, dust, paint chips, sand grains, insects, and any foreign object that becomes trapped in the eye. Those skilled in the art, in light of the present teachings, will recognize that users who stare into computer screens for long durations or work in work places where small debris is ubiquitous may benefit from the present invention. This may be effective in partially elimination glaucoma.

In some embodiments, the device may be configured to engage a section of the organ, such as the cornea of an eye, where the debris resides. However, when engaging other organs, the device may partially penetrate the organ or form a tight compressive junction around a periphery of the organ. Through the use of a vacuum that creates the suction, the device may pull the debris out of a sensitive, soft organ without the use of a liquid to help flush the debris from the organ. The device may be carried and use daily without the need for a physician. The portable, power independent nature of the device enables daily usage of the device to maintain optical hygiene and health.

In some embodiments, the device may include a vacuum portion 102 that generates a vacuum for sucking the debris from the organ. The generated suction pressure may be sufficient to pull debris from the organ without the use of a liquid or instrument to help in the process. In one embodiment, the suction pressure is solely sufficient for removal of the debris. The vacuum portion may include an internal diaphragm that expands to reduce the pressure within. The reduced pressure may create a partial vacuum, which is filled by air pushed in by atmospheric pressure. However in other embodiments, other mechanisms to create the suction may be utilized by the vacuum portion. For example, a manual hand pump may be used to generate the suction. The vacuum portion may be sized and dimensioned to fit inside a pocket. Suitable materials for the vacuum portion may include, without limitation, metal, rigid polymers, polyurethane, antibacterial polymers, cloth, and silicone. The vacuum portion may be powered by a power source. The power source may include an AC/DC compatible power socket, a battery, a rechargeable battery pack, water power, and a solar panel.

In some embodiments, a tube 104 may extend from the vacuum section towards the organ. The tube may be utilized to carry the debris from the organ to a debris storage portion of the vacuum portion. The vacuum portion may further include a debris storage portion (not shown) configured to catch and store the debris. The tube may be sufficiently long, such that the vacuum portion can be operated at a distance from the organ. Suitable materials for the tube may include flexible materials such as, but not limited to, plastic, polyurethane, and a woven fiber. The tube may be transparent to enable viewing of the debris passing through, and also to detect clogging inside the tube.

In some embodiments, an organ engagement portion 106 may join with the organ, over a section where the debris resides. The organ engagement portion may include an eye cup that is sized and dimensioned to engage a periphery of the eye. The organ engagement portion may include a rim 108 that is sized and dimensioned to seal the organ engagement portion against the surface of the organ. Those skilled in the art will recognize that a tight seal is necessary to sustain the suction pressure needed to pull the debris from the organ. The rim and the organ engagement portion may be treated with an antimicrobial solution to inhibit the growth of bacteria.

Figure 2:
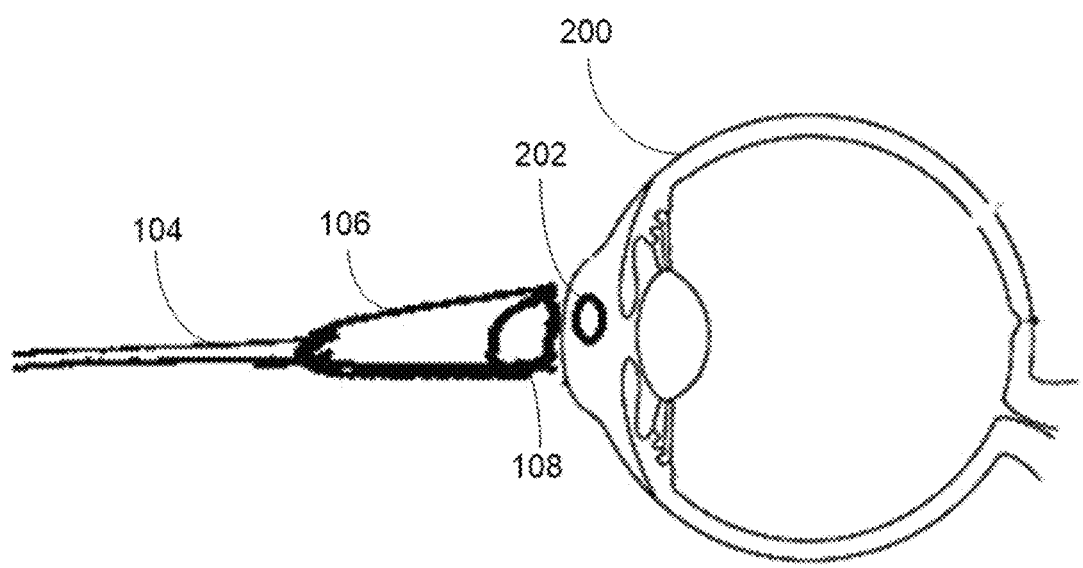
FIG. 2 illustrates a side view of an exemplary suction device engaging an exemplary organ to remove an exemplary debris, in accordance with an embodiment of the present invention.

FIG. 2 illustrates a side view of an exemplary suction device engaging an exemplary organ to remove an exemplary debris, in accordance with an embodiment of the present invention. In the present invention, debris 202 is sucked from an organ 200, through the organ engagement portion, through the tube, and finally into the debris storage portion of the vacuum portion. The organ may include, without limitation, an eye, a nose, an ear, a mouth, a liver, and an ear. In one embodiment, the rim may form a tight compression with a periphery of the eye, positing directly over the cornea of an eye, where the debris resides. Through the use of a vacuum that creates the suction, the device may pull the debris out of a sensitive, soft organ without the use of a liquid to help flush the debris from the organ. The device may be carried and use daily without the need for a physician.

In one alternative embodiment, the device may at least partially penetrate an organ to suck out debris. The rim may have a sharp edge that penetrates the organ. In another alternative embodiment, the organ engagement portion may have a camera for capturing an image of the organ in close up. In yet another alternative embodiment, the device has more than one tube to suck debris from multiple organs simultaneously. In another alternative embodiment, the device may be wall mounted. In yet another alternative embodiment, the device may be controlled by a satellite.

Those skilled in the art will readily recognize, in light of and in accordance with the teachings of the present invention, that any of the foregoing steps may be suitably replaced, reordered, removed and additional steps may be inserted depending upon the needs of the particular application. Moreover, the prescribed method steps of the foregoing embodiments may be implemented using any physical and/or hardware system that those skilled in the art will readily know is suitable in light of the foregoing teachings. For any method steps described in the present application that can be carried out on a computing machine, a typical computer system can, when appropriately configured or designed, serve as a computer system in which those aspects of the invention may be embodied. Thus, the present invention is not limited to any particular tangible means of implementation.

It will be further apparent to those skilled in the art that at least a portion of the novel method steps and/or system components of the present invention may be practiced and/or located in location(s) possibly outside the jurisdiction of the United States of America (USA), whereby it will be accordingly readily recognized that at least a subset of the novel method steps and/or system components in the foregoing embodiments must be practiced within the jurisdiction of the USA for the benefit of an entity therein or to achieve an object of the present invention. Thus, some alternate embodiments of the present invention may be configured to comprise a smaller subset of the foregoing means for and/or steps described that the applications designer will selectively decide, depending upon the practical considerations of the particular implementation, to carry out and/or locate within the jurisdiction of the USA. For example, any of the foregoing described method steps and/or system components which may be performed remotely over a network (e.g., without limitation, a remotely located server) may be performed and/or located outside of the jurisdiction of the USA while the remaining method steps and/or system components (e.g., without limitation, a locally located client) of the forgoing embodiments are typically required to be located/performed in the USA for practical considerations. In client-server architectures, a remotely located server typically generates and transmits required information to a US based client, for use according to the teachings of the present invention. Depending upon the needs of the particular application, it will be readily apparent to those skilled in the art, in light of the teachings of the present invention, which aspects of the present invention can or should be located locally and which can or should be located remotely. Thus, for any claims construction of the following claim limitations that are construed under 35 USC § 112 (6) it is intended that the corresponding means for and/or steps for carrying out the claimed function are the ones that are locally implemented within the jurisdiction of the USA, while the remaining aspect(s) performed or located remotely outside the USA are not intended to be construed under 35 USC § 112 (6).

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

It is noted that according to USA law 35 USC § 112 (1), all claims must be supported by sufficient disclosure in the present patent specification, and any material known to those skilled in the art need not be explicitly disclosed. However, 35 USC § 112 (6) requires that structures corresponding to functional limitations interpreted under 35 USC § 112 (6) must be explicitly disclosed in the patent specification. Moreover, the USPTO's Examination policy of initially treating and searching prior art under the broadest interpretation of a "mean for" claim limitation implies that the broadest initial search on 112(6) functional limitation would have to be conducted to support a legally valid Examination on that USPTO policy for broadest interpretation of "mean for" claims. Accordingly, the USPTO will have discovered a multiplicity of prior art documents including disclosure of specific structures and elements which are suitable to act as corresponding structures to satisfy all functional limitations in the below claims that are interpreted under 35 USC § 112 (6) when such corresponding structures are not explicitly disclosed in the foregoing patent specification. Therefore, for any invention element(s)/structure(s) corresponding to functional claim limitation(s), in the below claims interpreted under 35 USC § 112 (6), which is/are not explicitly disclosed in the foregoing patent specification, yet do exist in the patent and/or non-patent documents found during the course of USPTO searching, Applicant(s) incorporate all such functionally corresponding structures and related enabling material herein by reference for the purpose of providing explicit structures that implement the functional means claimed. Applicant(s) request(s) that fact finders during any claims construction proceedings and/or examination of patent allowability properly identify and incorporate only the portions of each of these documents discovered during the broadest interpretation search of 35 USC § 112 (6) limitation, which exist in at least one of the patent and/or non-patent documents found during the course of normal USPTO searching and or supplied to the USPTO during prosecution. Applicant(s) also incorporate by reference the bibliographic citation information to identify all such documents comprising functionally corresponding structures and related enabling material as listed in any PTO Form-892 or likewise any information disclosure statements (IDS) entered into the present patent application by the USPTO or Applicant(s) or any $3^{rd}$ parties. Applicant(s) also reserve its right to later amend the present application to explicitly include citations to such documents and/or explicitly include the functionally corresponding structures which were incorporate by reference above.

Thus, for any invention element(s)/structure(s) corresponding to functional claim limitation(s), in the below claims, that are interpreted under 35 USC § 112 (6), which is/are not explicitly disclosed in the foregoing patent specification, Applicant(s) have explicitly prescribed which documents and material to include the otherwise missing disclosure, and have prescribed exactly which portions of such patent and/or non-patent documents should be incorporated by such reference for the purpose of satisfying the disclosure requirements of 35 USC § 112 (6). Applicant(s) note that all the identified documents above which are incorporated by reference to satisfy 35 USC § 112 (6) necessarily have a filing and/or publication date prior to that of the instant application, and thus are valid prior documents to incorporated by reference in the instant application.

Having fully described at least one embodiment of the present invention, other equivalent or alternative methods of implementing a suction device that removes debris from organs according to the present invention will be apparent to those skilled in the art. Various aspects of the invention have been described above by way of illustration, and the specific embodiments disclosed are not intended to limit the invention to the particular forms disclosed. The particular implementation of the suction device that removes debris from organs may vary depending upon the particular context or application. By way of example, and not limitation, the suction device that removes debris from organs described in the foregoing were principally directed to a device that forms a seal with a periphery of the eye for sucking out debris therefrom implementations; however, similar techniques may instead be applied to sucking foreign debris from other organs, beyond the eye, which implementations of the present invention are contemplated as within the scope of the present invention. The invention is thus to cover all modifications, equivalents, and alternatives falling within the spirit and scope of the following claims. It is to be further understood that not all of the disclosed embodiments in the foregoing specification will necessarily satisfy or achieve each of the objects, advantages, or improvements described in the foregoing specification.

Claim elements and steps herein may have been numbered and/or lettered solely as an aid in readability and understanding. Any such numbering and lettering in itself is not intended to and should not be taken to indicate the ordering of elements and/or steps in the claims.

The corresponding structures, materials, acts, and equivalents of all means or step plus function elements in the claims below are intended to include any structure, material, or act for performing the function in combination with other claimed elements as specifically claimed.

The Abstract is provided to comply with 37 C.F.R. Section 1.72(b) requiring an abstract that will allow the reader to ascertain the nature and gist of the technical disclosure. It is submitted with the understanding that it will not be used to limit or interpret the scope or meaning of the claims. The following claims are hereby incorporated into the detailed description, with each claim standing on its own as a separate embodiment.

What is claimed is:

1. An apparatus comprising:
   A portable vacuum portion, said portable vacuum portion being configured to be operable for generating the vacuum force for sucking or suctioning eye debris, in which said portable vacuum portion comprises:
   a manual hand pump, wherein said manual hand pump is configured to be operable for generating the vacuum force;
   a diaphragm implement that is operable to expand to reduce a pressure within said portable vacuum portion,
   at least one of, an antibacterial polymer material and a silicone material; and
   a debris storage portion that is configured to be operable for catching or storing debris;
   a tube implement extending a distance from said vacuum portion, said tube implement being configured to be operable for carrying the eye debris to said debris storage portion for storage therein,
   in which said tube implement comprises:
      a transparent tube implement, wherein said transparent tube implement being configured to enable viewing of the debris passing through said tube implement and being operable for visually detecting clogging inside said transparent tube implement; and
      at least one of, a plastic material, a polyurethane material, and a woven fiber material;
   and
   an organ engagement portion that is configured to be into engagement with a distal end of said transparent tube implement, said organ engagement portion comprises:
      an eye cup, said eye cup being configured to be operable for removal of the eye debris with said vacuum force.

2. The apparatus as recited in claim 1,
   further comprising at least a rim portion joined to a distal end of said organ engagement portion, said rim portion being configured to be operable for removably sealing said organ engagement portion.

3. The apparatus as recited in claim 2, wherein the reduced pressure is configured to be operable for creating a partial vacuum.

4. The apparatus as recited in claim 3, in which said eye cup is further configured to engage a periphery of an eye.

5. The apparatus as recited in claim 1, in which said tube implement further comprises a flexible material.

6. The apparatus as recited in claim 3, in which said tube implement comprises at least a rim segment that is configured to seal said organ engagement portion against a surface of the organ.

7. The apparatus as recited in claim 1, in which said organ engagement portion is treated with an antimicrobial solution.

8. The apparatus as recited in claim 6, in which said rim portion is treated with an antimicrobial solution.

9. The apparatus as recited in claim 1, in which said eye cup is sized and dimensioned to engage a periphery of an eye.

10. The apparatus as recited in claim 8, in which said rim portion comprises a sharp edge operable for penetrating an organ.

11. The apparatus as recited in claim 9, in which the eye debris comprises objects trapped at a portion of a surface of the eye.

12. The apparatus as recited in claim 9, in which said organ engagement portion further comprises a camera for capturing an image of an eye.

13. The apparatus as recited in claim 1, in which the apparatus is configured for use without assistance.

14. An apparatus consisting of:
   a vacuum portion being configured to be operable for generating a vacuum force for sucking or suctioning eye debris;
   said vacuum portion comprises an internal diaphragm that is operable to expand to reduce a pressure within said vacuum portion;
   said vacuum portion further comprises a manual hand pump;
   said vacuum portion further comprises a debris storage portion;
   in which said vacuum portion is further configured to fit within a pocket,
   a tube implement, said tube implement comprises a flexible and transparent material,
      wherein said transparent tube implement is configured to be operable for enabling a viewing of the debris passing through said tube implement and for detecting a clogging inside said tube implement,
      said tube implement being further configured to be operable for carrying the debris sucked or suctioned by said vacuum force to said debris storage portion for storage therein;
   an eye engagement portion, said eye engagement portion comprises an eye cup shape, wherein said eye engagement portion being configured to be operable for engaging a distal end of said tube implement, in which said eye engagement portion comprises an antimicrobial solution; and
   a rim portion, said rim portion being disposed at a distal end of said eye engagement portion, wherein said rim portion being configured to be operable for removably sealing said eye engagement portion, and
   in which said apparatus comprises a portable apparatus.

* * * * *